US006501286B1

(12) United States Patent
Balfanz et al.

(10) Patent No.: US 6,501,286 B1
(45) Date of Patent: Dec. 31, 2002

(54) MULTIPLE REFERENCE ELECTRODE ARRAY FOR MEASURING OPEN CIRCUIT POTENTIALS IN ARTIFICIAL CREVICES

(75) Inventors: Robert W. Balfanz, Caledonia, WI (US); James E. Buhler, Waterford, WI (US); W. Stephen Tait, Madison, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 09/940,027

(22) Filed: Aug. 27, 2001

(51) Int. Cl.$^7$ .................................................. G01N 27/42

(52) U.S. Cl. ...................... 324/700; 324/71.1; 324/446; 204/404; 205/775.5

(58) Field of Search ................................ 324/700, 71.1, 324/446, 447, 609, 444; 204/404, 412; 205/775.5

(56) References Cited

U.S. PATENT DOCUMENTS 3,599,090 A 8/1971 Fitzpatrick et al. ....... 324/71 C
3,633,099 A 1/1972 Richman .................. 324/71 C
3,924,175 A 12/1975 Wilson ...................... 324/30 R
4,181,882 A 1/1980 Isaacs et al. .............. 324/71 R
4,285,232 A 8/1981 Garner .......................... 73/86
4,488,939 A 12/1984 Fu ............................. 204/1 T
5,517,851 A 5/1996 Berthold ........................ 73/87
5,865,971 A 2/1999 Sunkara ...................... 204/404

*Primary Examiner*—N. Le
*Assistant Examiner*—Vincent Q. Nguyen

(57) ABSTRACT

An electrode array device for use with a conductive element to simulate a crevice that is subject to corrosive conditions. The device includes a non-conductive member and a plurality of electrodes. The non-conductive member has a face, with the member defining (i) an opening through the member, the opening passing through the face of the member, and (ii) a depression formed in the face and contiguous with at least a portion of the opening. The plurality of electrodes is embedded in the member, with each of the plurality of electrodes having a portion exposed from the member to the depression.

16 Claims, 5 Drawing Sheets

MULTIPLE REFERENCE ELECTRODE ARRAY FOR MEASURING OPEN CIRCUIT POTENTIALS IN ARTIFICIAL CREVICES

FIELD OF THE INVENTION

This invention relates generally to studying crevice corrosion. More particularly, this invention relates to a multiple-reference electrode array for measuring open circuit potentials in artificial aerosol container crevices.

BACKGROUND OF THE INVENTION

A common problem associated with commercial aerosol containers is that the metals (e.g., tinplated steel, aluminum or the like) used to form the containers are susceptible to corrosion. The potential for corrosion depends, at least partially, on both the material used to construct the container and the medium (e.g., solution) provided in the container. Generally, the materials used to construct such containers are subject to a uniform amount of corrosion along their inner surfaces. However, in cracks and crevices formed in the containers, there occurs non-uniform corrosion that manifests itself in the form of, for example, pitting. In addition, the non-uniform corrosion occurring in the cracks and crevices generally takes place at a faster rate than at exposed surfaces in the containers.

In order to determine the long-term viability of materials to be used in aerosol containers containing particular solutions, or other environments in which crevice corrosion is a factor, it is necessary to accurately predict the rate of corrosion that will occur within the crevices. However, traditional techniques for measuring corrosion on open/exposed surfaces are generally inadequate for predicting crevice corrosion.

Techniques have been developed to gage corrosion in artificial crevices of varying geometry in order to provide a model for what could be expected in an actual crevice due to the materials and solutions forming the crevice environment. In such conventional devices, an electrode is typically provided in the artificial crevice to measure electrical properties in the crevice that are indicative of corrosion. Alternatively, some devices employ a crevice formed in an electrode itself. Examples of devices employing these conventional techniques for measuring crevice corrosion are described in U.S. Pat. Nos. 3,633,099, 4,181,882 and 3,599,090.

Unfortunately, conventional devices for corrosion analysis in artificial crevices have certain drawbacks. In particular, the known devices typically measure only a general likelihood of corrosion in the entire crevice. Thus, the known devices only take into account corrosion effects due to the diffusion of solutions from the bulk of a container into a crevice as a whole. However, in real-world applications, diffusion of a solution not only occurs from the main cavity of a container into a crevice, but may also occur within the crevice. Thus, corrosion may occur at different rates at different positions within the crevice. Conventional devices are not equipped to measure varying corrosion rates within a continuous crevice.

Another drawback of conventional crevice-corrosion analysis is its inflexibility to simulate accurately varying real-world environments. Different lines of containers will have crevices of different dimensions. However, conventional devices are not equipped to take into account the different aspect ratios (i.e., the crevice depth divided by the crevice width) of crevices occurring in different lines of commercial containers.

SUMMARY OF THE INVENTION

This invention is directed to a device designed to overcome the problems of the conventional devices, by allowing for a plurality of measurements related to corrosion within a single crevice, to take into account the complexities of the dimensions of the crevice.

Typically, the invention relates to measuring crevice corrosion in a test cell designed to simulate the corrosive conditions that exist inside a container. The test cell can be filled with a particular test solution. An artificial crevice, formed of a particular test material, is exposed to the test solution in the test cell in order to simulate the corrosive conditions occurring in cracks and crevices of a container.

In one aspect, the invention is directed to a novel member used to simulate a crevice in a test cell. Preferably, the member is provided with a plurality of electrodes for measuring crevice corrosion in a more comprehensive and accurate manner than with known designs. In another aspect, the invention is directed to a test cell using the crevice simulation member discussed above.

More specifically, in a preferred aspect, the device of the present invention includes a non-conductive member having a face with a depression formed therein. When the face of the member is placed against a test surface, the depression forms a simulated crevice between the member and the test surface. A plurality of electrodes is embedded in the non-conductive member. Each of the plurality of electrodes has a portion exposed to the depression.

Preferably, this invention is directed to an electrode array device that includes a non-conductive member having a face. The member defines (i) an opening through the member, the opening passing through the face of the member, and (ii) a depression formed in the face and contiguous with at least a portion of the opening. The device also includes a plurality of electrodes embedded in the member. Each of the plurality of electrodes has a portion exposed from the member to the depression.

In another embodiment, the invention is directed to an electrode array for measuring corrosion in a crevice. The electrode array includes a ring-shaped non-conductive member and a plurality of electrodes. The ring-shaped non-conductive member has a first face and a second face, and defines an opening therethrough extending through the first face and the second face. The first face defines an annular depression that is contiguous with the opening in the non-conductive member. The plurality of electrodes is embedded in the non-conductive member. Each of the plurality of electrodes has a portion exposed from the non-conductive member in the depression of the first face.

This invention can also be directed to a test cell for measuring corrosion in a crevice. The test cell includes a container, an electrode array, and a test electrode. The container preferably includes a valve assembly opening into the container. The electrode array device includes a non-conductive member and a plurality of electrodes. The non-conductive member has a face, with the member defining (i) an opening through the member, the opening passing through the face of the member, and (ii) a depression formed in the face and contiguous with at least a portion of the opening. The plurality of electrodes is embedded in the member, with each of the plurality of electrodes having a portion exposed from the member to the depression. The test electrode is sealingly secured to the face of the non-conductive member and is spaced from a surface of the depression therein to form the crevice. The container, electrode array device, and test electrode are sealingly secured together such that the crevice and an interior of the container are in flow communication.

These and other objects, features and advantages of the invention will be made apparent from the following description with reference to the drawings, in which like reference numerals refer to like elements throughout.

DETAILED DESCRIPTION OF THE PREFERRED EMBODIMENTS

Figure 1:
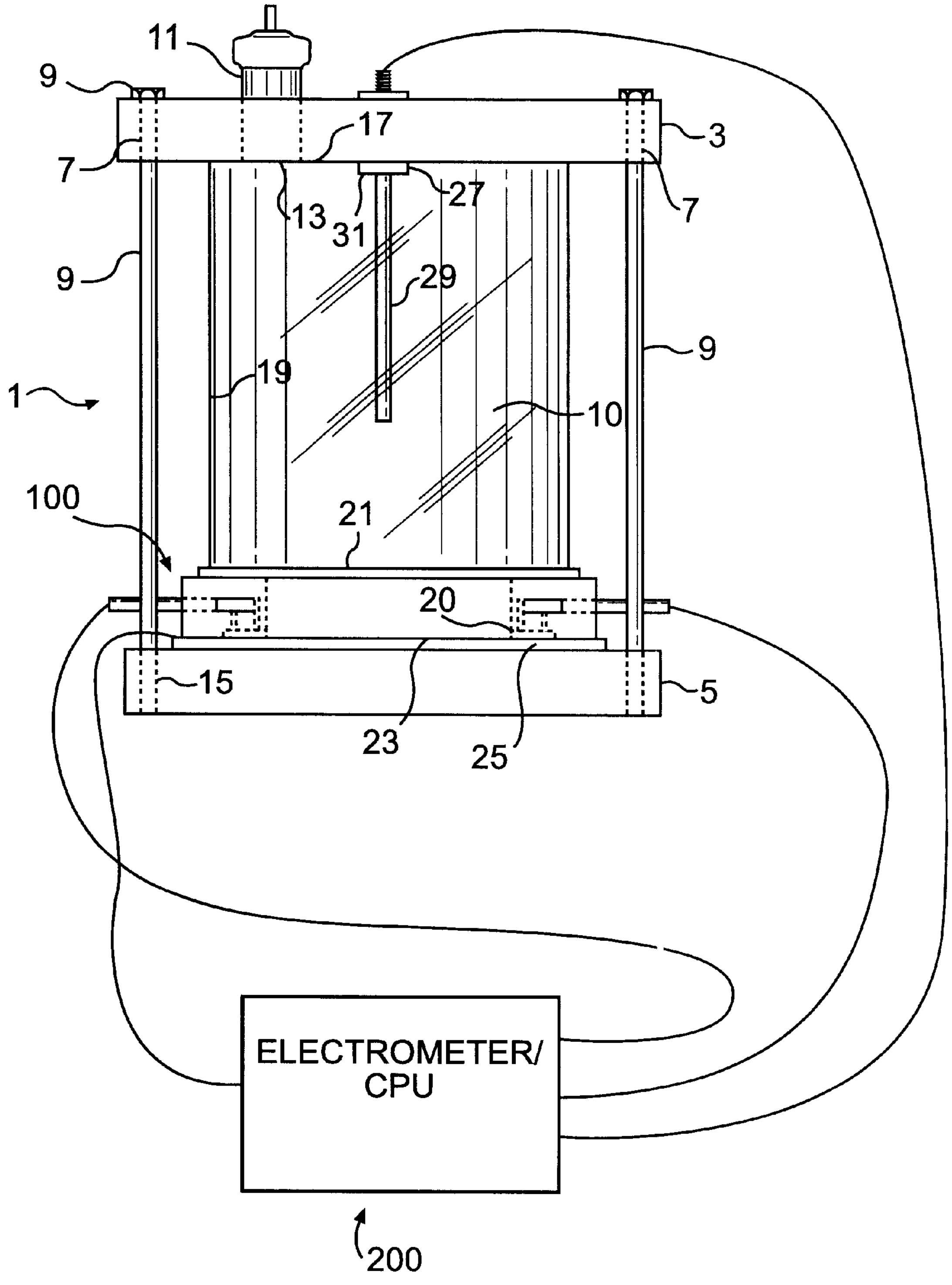
FIG. 1 is an elevational view of a test cell according to an embodiment of the present invention.

Our invention is generally used for measuring electrochemical activity in an artificial crevice, preferably by way of measuring open circuit potentials. An artificial crevice, as described above, provides a model of an actual crevice that is in flow communication with a main cavity of a commercial solution-containing container, such as an aerosol can, in order to measure corrosion that can occur due to the interaction between the solution and the material of the container. FIG. 1 illustrates a test cell 1 embodying one aspect of the invention. Test cell 1 defines a cavity, which is provided for containing a test solution, and which is in fluid communication with an artificial crevice. Although described and illustrated in conjunction with modeling crevices in commercial aerosol containers, this invention is not limited to testing directed to commercial aerosol containers, and is effective for measuring crevice corrosion for any number of environments in which such corrosion is a problem, including, but not limited to other containers, such as trigger sprayer products and the like, as well as other applications such as processing equipment.

The artificial crevice to be tested is preferably formed by fixing a test electrode to a face of a non-conductive member, the face including a depression. The test electrode forms a seal with the surface of the face of the non-conductive member at positions peripheral to the depression formed in the face. The test electrode is spaced from the surface of the depression to form the crevice, which preferably is in flow communication with an opening that passes through the non-conductive member. The crevice formed between the surface of the depression and the test electrode mimics the environment within crevices or cracks in a commercial aerosol can or the like.

Thus configured, the electrode array and test electrode may be used to measure electrochemical activity (e.g., open circuit potentials) in the crevice using conventional techniques, in order to produce an acceptable model of crevice corrosion.

Most commonly, the electrode array of this invention will be used in conjunction with a test electrode and an electrochemical corrosion test cell, as generally described above. Such test cells are known in the art as providing a model for the internal environment of an aerosol can or other container, or an environment susceptible to corrosion. When assembled, the test cell, electrode array, and test electrode may provide a sealed environment in which an aerosol, or other solution, may be introduced to simulate the environment within an aerosol can or the like. The solution may flow freely into the crevice formed between the non-conductive member and the test electrode. The plurality of electrodes in the non-conductive member provides a plurality of reference points to measure electrochemical activity within the crevice to determine corrosion.

Non-Conductive Member Housing the Plurality of Electrodes

Preferably, the non-conductive member housing the plurality of electrodes is shaped so as to mimic the shape of the simulated environment. In the case of a typical commercial aerosol can, the non-conductive member should be ring-shaped. However, it should be understood that this invention can be used to simulate crevice corrosion in a number of different environments. Accordingly, the non-conductive member may be shaped as appropriate for the simulation.

The non-conductive member has an opening extending through it from one face to another face that allows for flow communication between the main cavity of the test cell and the artificial crevice. In one face is formed the depression for forming the crevice.

By way of example, in order to mimic a commercial aerosol container, the non-conductive member can be annular, with an outer diameter in a range of about 3 to 4 in., and an inner diameter in a range of about 1 to 1.75 in. The width of the non-conductive member, between opposing first and second faces (measured at its perimeter, not a depression surface) is preferably in the range of about 0.5 to 1 in. Again, however, the shape and size of the non-conductive member may be varied to simulate different environments and to conform to the test cell with which it may be used.

In the preferred ring-shaped, non-conductive member housing the plurality of electrodes, the depression is formed in the first face of the member. The depression is also ring-shaped and contiguous with the entire inner circumference of the first face of the non-conductive member. The depth and width of the depression may be varied to simulate differently sized crevices that occur in different commercial containers. For example, the crevice can be formed to approximate the mean aspect ratio of any of a number of actual aerosol containers. A majority of common aerosol containers can be simulated by aspect ratios falling in the range of about 1.5 to about 6.

The depression is formed such that a width of the non-conductive member from the top of the first face to the second face is greater than a width from the surface of the depression of the first face to the second face. Preferably, the depth of the depression is uniform with respect to a peripheral surface of the first face, such that the surface of the depression and the peripheral surface of the first face are substantially parallel, and are separated from each other by a step, lip, or the like. However, the depression may be formed in other configurations. For instance, the depression may be progressively formed in the first face and may have varying depths.

The first face (at portions peripheral to the depression) and second face of the non-conductive member are preferably flat so as more easily to allow an airtight seal to be formed with a test electrode, test cell, or other component. In more preferred embodiments, O-rings, flat gaskets, and the like may be provided to ensure that proper seals are formed. In such cases, the non-conductive member may have recesses formed therein to couple the gaskets or O-rings.

When an O-ring or flat gasket is used to provide a seal between the first face of the non-conductive member and the test electrode, the depth of the crevice may be manipulated by the spacing provided by the gasket or ring between the first face and the test electrode.

The non-conductive member is preferably formed of a plastic or an epoxy substance such as an epoxy resin and acrylate ester blend. The non-conductive member may be formed using any conventional method, including injection molding or using an SLA (stereolithograph apparatus) process.

Array of Electrodes

The plurality of electrodes (reference electrodes) embedded in the non-conductive member may be formed of any conventional conductive material used to construct electrochemical reference or pseudo-reference electrodes. Preferably, the electrodes are formed of hastelloy C-276 wire, or other material that spontaneously passivates in the desired test solution.

The reference electrodes are exposed to a crevice environment at the surface of the depression. Preferably, the exposed portions of the reference electrodes are substantially flush with the surface of the depression; however, in other embodiments, the electrodes may protrude out from or be recessed from the surface of the depression. The exposed portions of the various reference electrodes may be distributed about the surface of the depression. When the depression forms a closed loop, we prefer that the exposed portions of the reference electrodes be spaced circumferentially about the depression. We also prefer that the exposed portions of the electrodes be spaced at different distances from the opening through the non-conductive member (e.g., at different depths in the crevice). Thus, the array of electrodes may provide measurements at various positions within the artificial crevice formed by the depression of the non-conductive member and a surface to be tested (i.e., the test electrode). The exact position of the electrodes within the depression may be varied as necessary for a particular test model.

Preferably, the diameter of the exposed portion of each electrode of the plurality (for electrodes having a circular cross section at their exposed portions) is in the range of about 0.010 to about 0.040 in. We also prefer that the diameter of the exposed portion of the electrodes be less than half the distance between the exposed portion and a test electrode, when the electrode array and test electrode are assembled to form the artificial crevice for testing.

The electrodes may extend out from the non-conductive member to form an electrical connection with testing equipment (described in more detail below) at the outer periphery of the non-conductive member. However, the electrodes (or wires attached thereto) may extend out from the non-conductive member at any portion(s) thereof so long as they do not interfere with the testing environment.

The electrodes should be embedded in the non-conductive member such that aerosol or other solutions will not leak through any spaces formed between the length of the electrodes and the non-conductive member through which the electrodes extend. In preferred embodiments, widths of the electrodes (and corresponding widths of the passages formed in the non-conductive member through which the electrodes extend) are varied in a stepping fashion. The steps of each electrode and each corresponding passage complement each other so as to act as a seal preventing leakage. In other embodiments, epoxies or other sealing agents may be provided in or around the passages or electrodes to prevent leakage.

Test Electrode

The test electrode may be used to simulate the surface of the inside of a commercial aerosol container, or other surface potentially subject to corrosion. In preferred embodiments, a section of the actual material used (or being considered) to form a commercial aerosol can is used as the test electrode. Typical test electrodes include metals such as tinplated steel and aluminum. The surfaces of the test electrodes may have coatings formed thereon, in order to test the effectiveness of the coatings in preventing corrosion.

Preferably, the test electrode is wider than the opening through the non-conductive member and the depression formed in the first face, so as to provide an adequate seal with the non-conductive member. More preferably, the test electrode is wider, at least at a portion thereof, than the outer dimensions of the non-conductive member (to provide a contact surface for testing equipment, described below). However, this design may be varied to simulate various geometries of the surface(s) to be tested.

The test electrode may be electrically connected to testing equipment for quantifying the electrochemical environment of the crevice by, for example, an alligator clip-and-wire arrangement attached to an outer periphery of the test electrode. However, any conventional electrical connection may be made between the test electrode and the testing equipment.

Electrochemical Corrosion Test Cell

As discussed above, the test electrode and non-conductive member with a plurality of electrodes forming the electrode array are preferably used with an electrochemical corrosion test cell. Such test cells are known in the art for simulating environments such as the internal environment of a commercial aerosol container, in which electrochemical measurements are performed. The test cells are commercially available. For example, a Tait Cell, available from Perkin-Elmer (Oak Ridge, Tenn.), can be used for this invention. Other examples of such test cells include the Solatron 12852a and Pairodocs Professional Model Nos. 170 and 160 available.

A preferred test cell according to the invention provides, in conjunction with a non-conductive member (including a plurality of electrodes) and a test electrode, as described above, a container for receiving a solution to be tested.

A cavity of the container should be in flow communication with the opening extending through the non-conductive member, such that the solution in the cavity of the container may flow through the opening in the non-conductive member and into the crevice formed between the surface of the test electrode and the surface of the depression in the first face of the non-conductive member. The test electrode, non-conductive member (including the plurality of electrodes), and container should be sealingly secured to one another such that the aerosol or other solution used in the testing does not escape, and impurities from outside the enclosed environment do not penetrate the test cell.

In most preferred embodiments, the test cell includes a top plate and a bottom plate connected to each other by a nut-and-bolt arrangement. Between the two plates (which are preferably metal) may be positioned a cylinder (preferably glass), the non-conductive member containing the plurality of electrodes, and the test electrode. These pieces may be secured together by a biasing force created by the tightening of the nut-and-bolt arrangement secured to the two plates.

The top plate preferably has a first side against which the cylinder is sealingly biased. The first side of the top plate may be provided with a cylindrical groove coupling the cylinder, a flat gasket or other sealing member for providing a leak-tight seal between the top plate and the cylinder, and a non-conductive coating so as to prevent electrical interference with the environment inside the test cell.

The cylinder may be clamped between the first side of the top plate and the second face of the non-conductive member containing the electrodes. A typical/preferred cylinder has a length in the range of about 3 to about 6 in. The cylinder may be biased against the second face of the non-conductive member such that the opening through the non-conductive member opens into the cylinder. Preferably, a flat gasket, O-ring, epoxy, silicon rubber, or the like may be provided between the cylinder and the non-conductive member, so as to provide an airtight seal. Shapes other than a cylinder also may be used, while still providing a cavity between the top plate and the non-conductive member.

The test electrode is biased against the first face of the non-conductive member by the bottom plate so as to form the artificial crevice with the depression formed in the non-conductive member. A seal may be formed at a portion of the first face peripheral to the depression. Preferably, the test electrode is flush against the peripheral portion of the first face, and spaced from the depression. Thus, a solution may flow through the opening in the non-conductive member and into the space between the depression surface and the test electrode (i.e., the crevice), up to the portions of the first face that are flush with the test electrode. An O-ring, flat gasket, silicon rubber, epoxy or the like may be provided between the non-conductive member and the test electrode to provide a leak-tight seal.

When the bottom plate is metallic, a non-conductive flap (e.g., rubber, plastic or the like) or coating may be provided between the test electrode and the bottom plate to prevent interference with the electrical connection of the test electrode.

The first plate typically houses an aerosol valve assembly or the like. The aerosol valve is crimped onto the assembly after a test solution is filled into the test cell, and then propellant is filled into the test cell through the aerosol valve.

In addition, another reference electrode may be provided in the test cell to provide a measurement of the open cell potential between a main portion of the test cell and a portion of the test electrode not positioned in the crevice. Preferably, the additional reference electrode sealingly protrudes through the first plate and extends into the interior of the test cell (i.e., to be positioned within the cavity). Measurements from the reference electrode may be used to provide baseline information (indicating non-crevice corrosion).

Thus configured, a solution may be introduced into the electrochemical corrosion test cell so as to measure electrochemical properties and/or circuit potentials in the crevice indicative of corrosion of the test electrode.

The test cell, of course, may be manipulated to provide different information. For instance, any one of a number of solutions may be introduced into the test cell to measure its effect on, for example, the open circuit potentials between the electrodes. Also, the test electrode may be interchanged to test the performance of different metals or alloys with a particular solution. In addition, the non-conductive member may be interchanged with other non-conductive members having different crevice dimensions.

Preferably, open circuit potentials between the various reference electrodes and the test electrode are measured. Typically, when measuring open circuit potentials, higher (more positive) open circuit potentials indicate that corrosion is less likely to occur. Lower (more negative) open circuit potentials indicate that corrosion is more likely to occur. The open circuit potentials may be measured using any conventional methods. Preferably, however, the electrodes are each connected to a high-impedance voltmeter (e.g., an electrometer or operational amplifier). Most preferably, a Keithley Model No. 617 is used as the electrometer.

All of the electrodes may be electrically connected to the electrometer. Open circuits may be alternately formed between each of the reference electrodes and the test electrode using a computer controller multiplexer such as a Keithley Model 7001 or 7002 multiplexer. The open circuit potentials measured for these open circuits by the electrometer may be recorded to analyze corrosion in the crevice. In the open circuits, different potentials are caused by the environment to which the metal is exposed. For example, the open circuit potential for steel in water could be −0.660 V, but the open circuit potential for the same steel in ethyl alcohol could be +0.200V.

Preferably, the electrometer is connected to a central processing unit (CPU) that measures, records, and analyzes the open circuit potentials.

Thus, the open circuit potential in any set of electrodes will be a function of factors such as (1) the geometry of the crevice in which the electrode is positioned, (2) the position within the crevice of the electrode, (3) the material forming the test electrode, and (4) the solution contained in the test cell.

The attached drawings show one embodiment of the present invention, as set forth below.

FIG. 1 shows test cell 1. Test cell 1 includes top plate 3 and bottom plate 5. Both top plate 3 and bottom plate 5 are constructed of metal, with their faces being square in shape. Top plate 3 includes holes 7 (two of four shown) positioned in each of the four comers of the square face. Holes 7 are adapted for receiving bolts 9 (two of four shown). Top plate 3 also includes hole 27 for receiving electrode 29. In addition, valve assembly 11 is positioned in top plate 3, such that valve assembly 11 can control the flow communication of gas therethrough. The bottom face of top plate 3 includes circular recess 13.

Bottom plate 5 includes holes 15 (two of four shown), which also receive bolts 9. Holes 15 are threaded so as to threadingly engage threaded free ends of bolts 9.

When assembled, bolts 9 extend through holes 7 in top plate 3 and threadingly engage holes 15 in bottom plate 5, so as to secure the plates in place. As bolts 9 are tightened, top plate 3 and bottom plate 5 are biased towards each other.

Also, when assembled, between top plate 3 and bottom plate 5 are positioned, in order from top plate 3 to bottom plate 5, first gasket 17, glass cylinder 19, second gasket 21, electrode array 100, test electrode 23 and insulator 25.

First gasket 17 is a ring-shaped rubber member formed to be positioned in recess 13. First gasket 17 is sized such that it contacts the circumference of the top of cylinder 19 so as to form an airtight seal between top plate 3 and cylinder 19, when those two parts are biased towards each other, but allows for flow communication between valve assembly 11 and cylinder 19.

Second gasket 21 is a ring-shaped rubber member shaped to contact the circumference of the bottom of cylinder 19 in order to form an airtight seal when molded member 130 of electrode array 100 and cylinder 19 are biased towards each other, while simultaneously allowing flow communication between cylinder 19 and opening 170 in electrode array 100.

Electrode array 100 is ring-shaped and formed of molded plastic, and has a plurality of electrodes positioned therein. (A more detailed description is provided below.)

Test electrode 23 contacts portions of the bottom face of electrode array 100 so as to form an airtight seal when the two are biased towards each other. A third ring-shaped gasket (not shown) is positioned on the bottom face of electrode array 100 and contacts test electrode 23 to aid in providing an airtight seal.

Test electrode 23 rests on top of insulator 25, which is formed of rubber, or another nonconductive material, and rests upon bottom plate 5. In the depicted embodiment, insulator 25 has a greater surface area than test electrode 23, which has a greater surface area than electrode array 100.

As bolts 9 are tightened, top plate 3 and bottom plate 5 are biased towards each other. This causes first gasket 17, cylinder 19, second gasket 21, electrode array 100, test electrode 23 and insulator 25 to be clamped between top plate 3 and bottom plate 5, defining a chamber within test cell 1.

Valve assembly 11 and hole 27 are in flow communication with a region defined by cylinder 9, when cylinder 19 is biased against gasket 17 in recess 13 of top plate 3. Valve assembly 11 is crimped on top plate 3 after test cell 1 is filled with a test fluid. Once sealingly secured to top plate 3, valve assembly 11 is used to introduce a propellant into the chamber of test cell 1.

Hole 27 is made to be airtight by inserting reference electrode 29 into hole 27. Reference electrode 29 is positioned in sealing member 31, which aids in sealingly securing reference electrode 29 in hole 27. Specifically, sealing member 31 is made of plastic and has an outer threaded portion. Hole 27 is also threaded, such that hole 27 and sealing member 31 threadingly engage each other to form an airtight seal. With reference electrode 29 being securely positioned in sealing member 31, when sealing member 31 is positioned in hole 27, electrode 29 protrudes into the chamber defined by cylinder 19.

Figure 2:
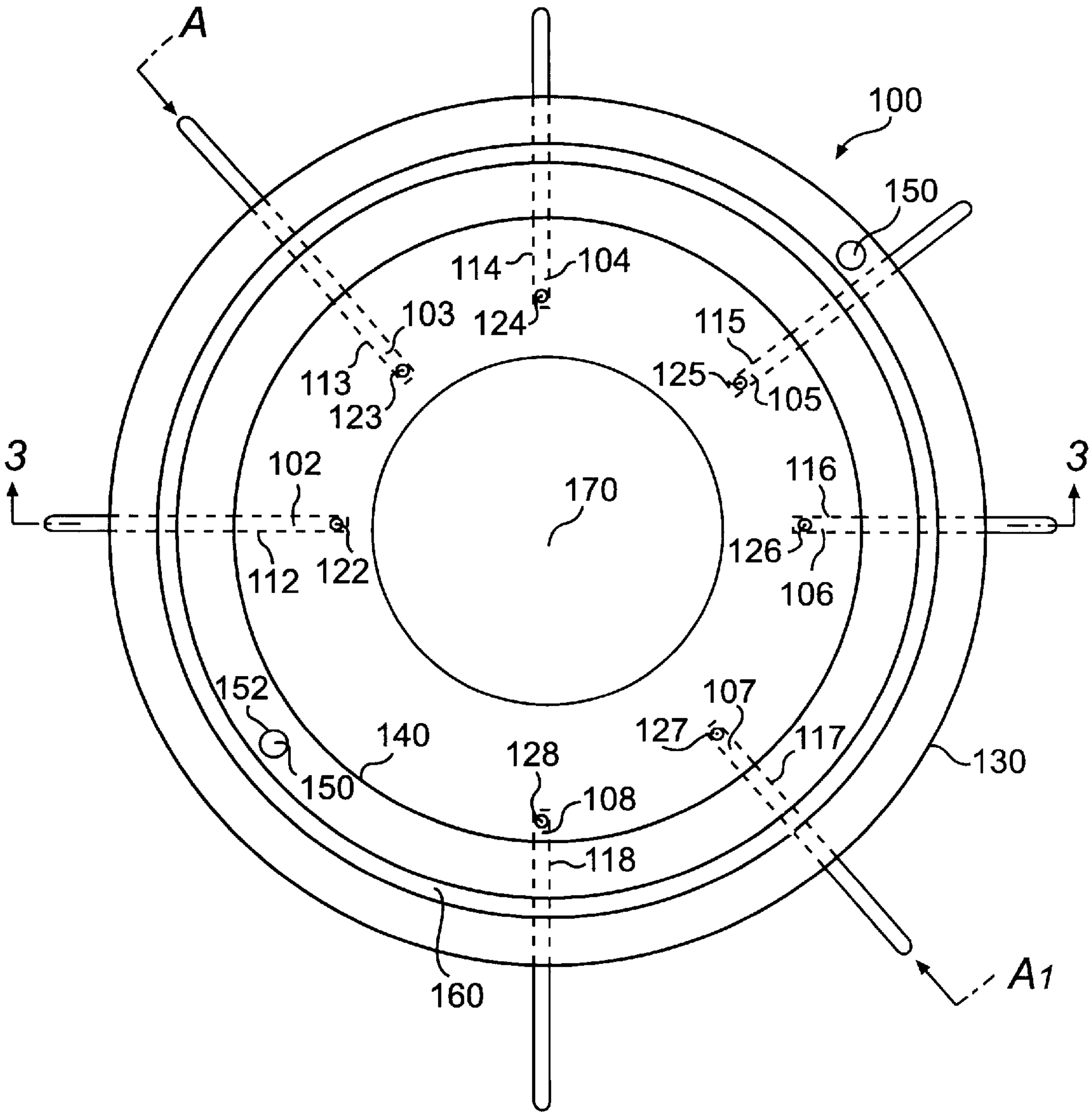
FIG. 2 is a top schematic view of an electrode array according to an embodiment of the present invention.
Figure 3:
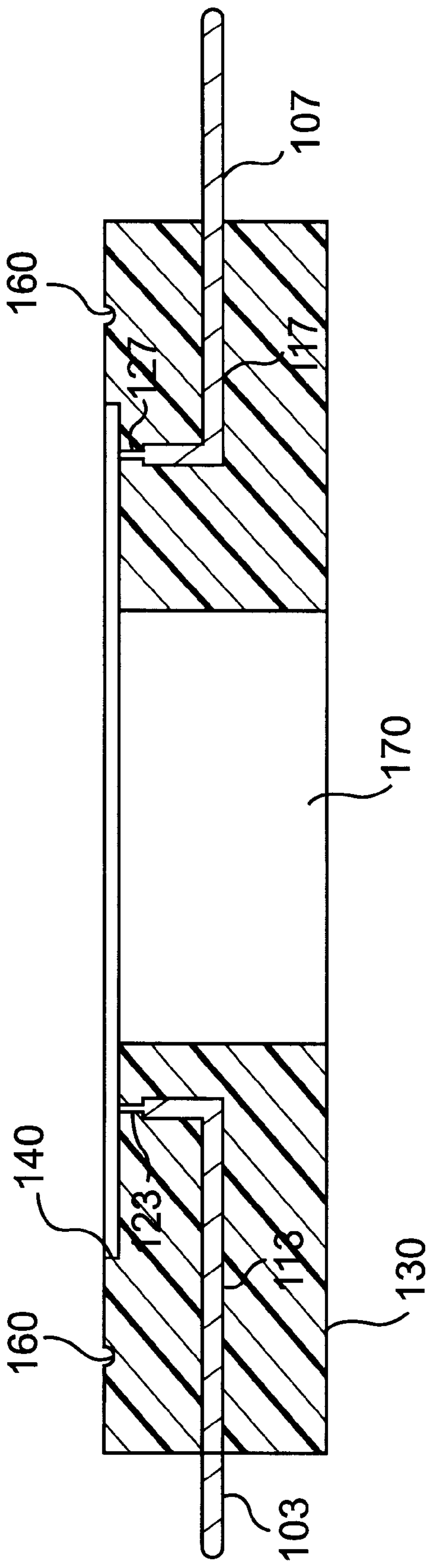
FIG. 3 is a side sectional view of the electrode array of FIG. 2 along line A–A1.

FIGS. 2 and 3 show top and side views, respectively, of electrode array 100. Electrode array 100 includes a plurality of electrodes 102 to 108, which are arranged in a clockwise manner around electrode array 100. Electrodes 102 to 108 extend through, and are positioned in, canals 112 to 118, respectively, in molded member 130. Canals 112 to 118 extend from outer side walls of molded member 130 to various positions within molded member 130, at which point the canals form a substantially right angle such that they extend from mid-points within the width of molded member 130, to the bottom face of molded member 130. At the bottom face of molded member 130, canals 112 to 118 form openings in the surface thereof. Electrodes 102 to 108 are positioned in canals 112 to 118 such that tips 122 to 128 of electrodes 102 to 108 are exposed from molded member 130 at the openings of canals 112 to 118 in the bottom face of molded member 130.

Tips 122 to 128 of the electrodes 102 to 108 are all exposed in a depressed portion of the bottom face of molded member 130. The depressed portion is defined by a circular step 140 formed in the bottom face of molded member 130, and extends to opening 170 (which extends through the center of molded member 130). Circular step 140 extends around a mid-portion of the bottom face of molded member 130, such that molded member 130 includes two substantially parallel surfaces on its bottom face. Thus constructed, the width of molded member 130 (measured from its bottom (first) face to its top (second) face) in the area from step 140 to opening 170 is less than the width of molded member 130 measured in the area from step 140 to the outer circumference of molded member 130.

The openings of canals 112 to 118, having tips 122 to 128 exposed therein, are positioned at various points around the circumference of the depression in the bottom face of molded member 130. Also, tips 122 to 128, and their respective openings, are spaced from opening 170 in a progressive manner such that tip 122 is the closest to opening 170 and tip 128 is furthest from opening 170. This arrangement allows for measurements by electrodes 102 to 108 at various positions in the depression.

Molded member 130 is formed by injection molding, with two separate molded pieces being formed. One of the molded pieces includes the top face and one of the molded pieces contains the bottom face, such that the two molded pieces form two separate ring-shaped members. The two pieces are secured together with electrodes 102 to 108 being positioned in canals 112 to 118. Metal posts 150 are positioned in cavities 152 in molded member 130, so as to extend across the seam of the separate portions of molded member 130 when secured. Metal posts 150 prevent the shifting of the separate portions with respect to one another.

Circular groove 160 defines a closed loop along the bottom face of molded member 130, at a position outside of the depression in the bottom face. Groove 160 is formed to couple the third gasket (not shown), which is placed therein. When the third gasket is positioned in groove 160, molded member 130 can more easily form an airtight seal with test electrode 23, when the two are biased against each other.

When test electrode 23 and molded member 130 are biased against each other, the portions of test electrode 23, including the third gasket, that come into contact with the bottom face of molded member 130, have positions peripheral to step 140. Accordingly, there is a space in the test electrode 23 between the bottom face of molded member 130 in the depression defined by step 140. This forms a crevice 20 between test electrode 23 and the bottom face of molded member 130 in the depression, which is in flow communication with opening 170.

Figure 4A:
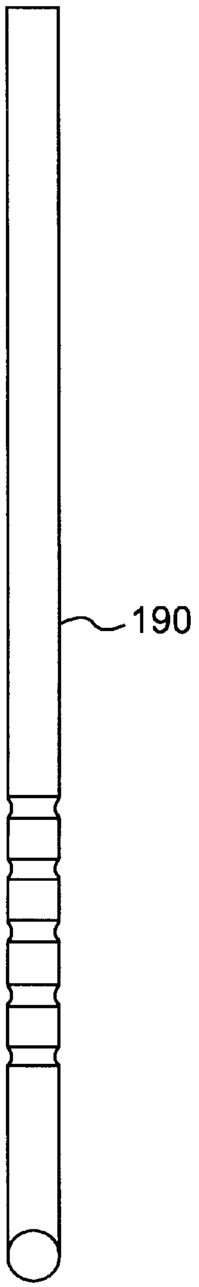
FIGS. 4A and 4B are front and side plan views, respectively, of a preferred electrode that may be used with the present invention.
Figure 4B:
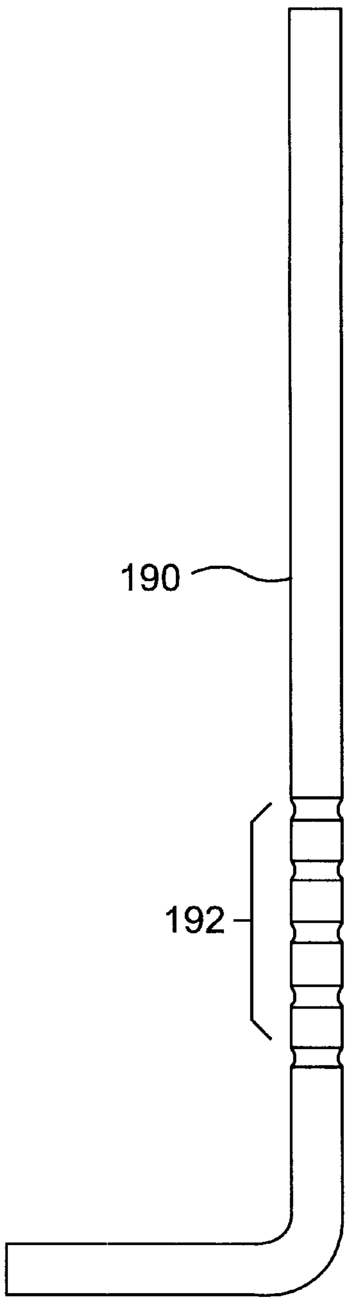

FIGS. 4A to 4B and 5A to 5B show individual electrodes which may be used with electrode array 100. FIGS. 4A and 4B show electrode 102, discussed in the present embodiment. Electrode 102 includes grooves 101, which are formed to receive epoxy, or the like, so as to ensure that there is formed an airtight seal between canal 112 and electrode 102.

Figure 5A:
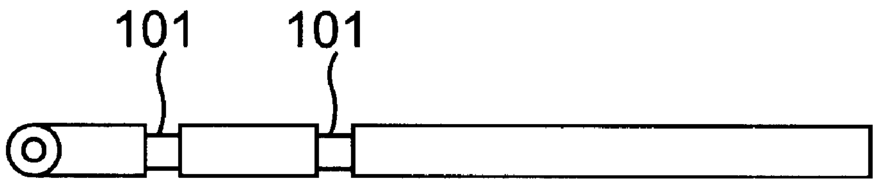
FIGS. 5A and 5B are front and side plan views, respectively, of another preferred electrode that may be used with the present invention.
Figure 5B:
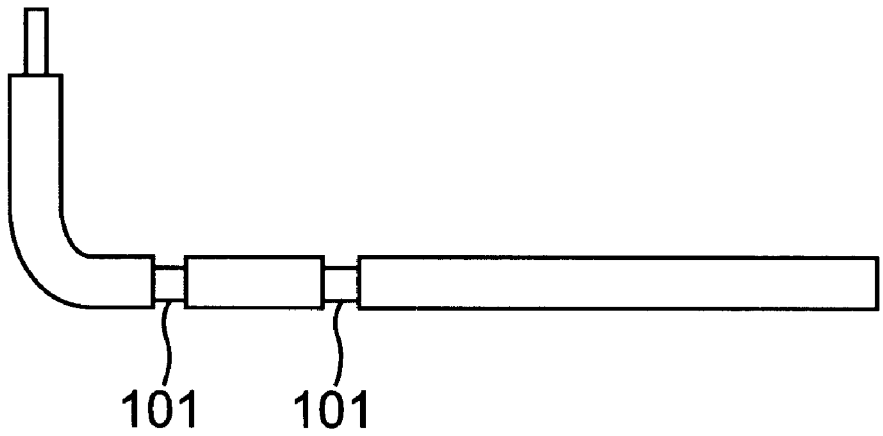

FIGS. 5A and 5B show electrode 190, which also may be used with the present invention. Grooves 192, similar to grooves 101 of electrode 102, are formed on the sides of electrode 190, so as to receive epoxy or the like to form a seal with a respective canal of molded member 130. No tip is formed in electrode 190, but rather, the electrode has a flat end that is to be exposed in the corresponding canal opening in the depression of molded member 130 of electrode array 100. The shape of canals 112 to 118 in molded member 130 may be varied so as to receive electrode 190.

Thus constructed, electrode array 100 is used in test cell 1 to measure electrochemical activity in the crevice 20 formed between the depression in the bottom face of molded member 130 and test electrode 23.

Free ends of electrodes 102 to 108, opposite to the ends having tips 122 to 128, are attached directly, or with conductive wiring, to electrometer/CPU 200. In addition, test electrode 23 is also electrically connected to electrometer/CPU 200 by conductive wiring. With such an arrangement, open circuits may be formed between electrodes 102 to 108 (preferably, one at a time) and test electrode 23, in order to measure the open circuit potentials in the crevice 20 formed between the bottom face of molded member 130 and test electrode 23. An open circuit potential is measured when a fluid, such as an aerosol or the like, is placed in the container of test cell 1, which is defined by top plate 3, cylinder 19, electrode array 100 and test electrode 23. The open circuit potential is indicative of the corrosion rate of test electrode 23 in the presence of the fluid placed in test cell 1.

Electrode 29 is a reference electrode electrically connected with electrometer/CPU 200 by conductive wiring or the like, and provides ground information to electrometer/CPU 200.

While the present invention has been described above with respect to what are considered to be preferred embodiments, the invention is not limited to the disclosed embodiments. To the contrary, the invention is intended to cover various modifications and equivalent arrangements included within the spirit and scope of the appended claims. The scope of the claims is to be accorded the broadest interpretation so as to encompass all such modifications and equivalent structures and functions.

INDUSTRIAL APPLICABILITY

The present invention is useful for testing materials to be used in aerosol containers and the like. In particular, the invention is particularly useful in creating crevice-like conditions which exist in typical aerosol containers and testing the resiliency of the material of which an aerosol container is to be constructed.

We claim:

1. An electrode array device for use with a conductive element to simulate a crevice that is subject to corrosive conditions, said device comprising:

a non-conductive member having a face, said member defining (i) an opening through said member, the opening passing through the face of said member, and (ii) a depression formed in the face and contiguous with at least a portion of the opening so as to create a simulated crevice between the face and the conductive element; and a plurality of electrodes, for measuring electrical potentials, embedded in said member, each of said plurality of electrodes having a portion exposed from said member to the depression.

2. The electrode array device according to claim 1, wherein the opening is substantially cylindrical, and said member substantially ring-shaped.

3. The electrode array device according to claim 2, wherein the exposed portion of each of said plurality of electrodes is spaced a different distance from an inner circumference of said member.

4. The electrode array device according to claim 1, wherein the depression is ring-shaped and contiguous around its entire inner perimeter with the opening.

5. The electrode array device according to claim 4, wherein the exposed portions of said plurality of electrodes are spaced circumferentially from each other around the depression, and at least two of the exposed portions are spaced at different distances from the opening.

6. The electrode array device according to claim 5, wherein said member is formed of a material selected from the group consisting of plastic, epoxy, and Delrin.

7. A method of measuring corrosion in the crevice using the electrode array device according to any one of claims 1 to 6, said method comprising the steps of:

providing a test solution in the crevice;

alternately forming an open circuit potential between each of the plurality of electrodes and the conductive element; and measuring the open circuit potential of each open circuit formed using the conductive element and each electrode of the plurality of electrodes.

8. A test cell for measuring corrosion in a crevice, said test cell comprising:

a container;

an electrode array device comprising:

(1) a non-conductive member having a face, said member defining (i) an opening through said member, the opening passing through the face of said member, and (ii) a depression formed in the face and contiguous with at least a portion of the opening; and (2) a plurality of electrodes embedded in said member, each of said plurality of electrodes having a portion exposed from said member to the depression; and a test electrode sealingly secured to the face of said non-conductive member and spaced from a surface of the depression therein to form the crevice, wherein said container, said electrode array device, and said test electrode are sealingly secured together such that the crevice and an interior of the container are in flow communication.

9. The test cell according to claim 8, wherein the opening is substantially cylindrical, and said member substantially ring-shaped.

10. The test cell according to claim 9, wherein the exposed portion of each of said plurality of electrodes is spaced a different distance from an inner circumference of said member.

11. The test cell according to claim 8, wherein the depression is ring-shaped and contiguous around its entire inner perimeter with the opening.

12. The test cell according to claim 11, wherein the exposed portions of said plurality of electrodes are spaced circumferentially from each other around the depression, and at least two of the exposed portions are spaced at different distances from the opening.

13. An electrode array for use with a conductive element to simulate a crevice that is subject to corrosive conditions, said electrode array comprising:

a ring-shaped non-conductive member having a first face and a second face, and defining an opening therethrough extending through the first face and the second face, wherein the first face defines an annular depression that is contiguous with the opening in said non-conductive member so as to create a simulated crevice between the first face and the conductive element; and a plurality of electrodes embedded in said non-conductive member, each of said plurality of electrodes having a portion exposed from said non-conductive member in the depression of the first face.

14. The electrode array device according to claim 13, wherein the opening is substantially cylindrical, and said member substantially ring-shaped.

15. The electrode array device according to claim 13, wherein the exposed portion of each of said plurality of electrodes is spaced a different distance from an inner circumference of said member.

16. The electrode array device according to claim 13, wherein the exposed portions of said plurality of electrodes are spaced circumferentially from each other around the depression, and at least two of the exposed portions are spaced at different distances from the opening.

* * * * *